United States Patent [19]

Bastian

[11] 4,024,265

[45] May 17, 1977

[54] BENZO[5,6]CYCLOHEPTA[1,2-C]PYRIDINES

[75] Inventor: Jean-Michel Bastian, Therwil, Switzerland

[73] Assignee: Sandoz Ltd., Basel, Switzerland

[22] Filed: Oct. 20, 1975

[21] Appl. No.: 623,777

[30] Foreign Application Priority Data

Oct. 24, 1974 Switzerland ............... 14240/74

[52] U.S. Cl. .................. 424/267; 260/293.54; 260/293.72; 260/293.81
[51] Int. Cl.² .................... C07D 221/16
[58] Field of Search .......... 260/293.54; 424/267

[56] References Cited

UNITED STATES PATENTS 3,573,316   3/1971   Ebnother et al. ............. 260/294.7
3,839,338  10/1974   Albertson et al. ............ 260/287 R Primary Examiner—G. Thomas Todd
Attorney, Agent, or Firm—Gerald D. Sharkin; Robert S. Honor; Timothy G. Rothwell

[57] ABSTRACT

This invention provides new compounds of formula I,

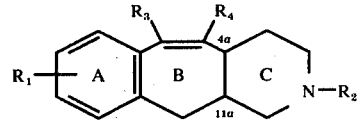

wherein
  $R_1$ is hydrogen, alkyl or 1 to 4 carbon atoms, fluorine, chlorine or bromine,
  $R_2$ is hydrogen, alkyl of 1 to 4 carbon atoms, cycloalkylalkyl of 4 to 10 carbon atoms, alkenyl or alkinyl of 3 to 6 carbon atoms, the multiple bond thereof being other than adjacent to the nitrogen atom of the tricyclic ring system, oxoalkyl of 2 to 5 carbon atoms, the oxygen atom thereof being separated by at least two carbon atoms from the nitrogen atom of the tricyclic ring system, or phenylalkyl of 7 to 10 carbon atoms,
  $R_3$ is hydrogen or alkyl of 1 to 4 carbon atoms,
  and $R_4$ is hydrogen or alkyl of 1 to 4 carbon atoms,
useful as antidepressants.

29 Claims, No Drawings

BENZO[5,6]CYCLOHEPTA[1,2-c]PYRIDINES

The present invention relates to benzo[5,6] cyclohepta[1,2-c]pyridines.

More particularly, this invention provides compounds of formula I

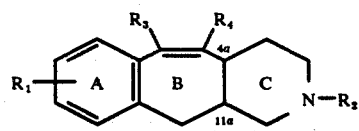

wherein
$R_1$ is hydrogen, alkyl or 1 to 4 carbon atoms, fluorine, chlorine, or bromine,
$R_2$ is hydrogen, alkyl of 1 to 4 carbon atoms, cycloalkylalkyl of 4 to 10 carbon atoms, alkenyl or alkinyl of 3 to 6 carbon atoms, the multiple bond thereof being other than adjacent to the nitrogen atom of the tricyclic ring system, oxoalkyl of 2 to 5 carbon atoms, the oxygen atom thereof being separated by at least two carbon atoms from the nitrogen atom of the tricyclic ring system, or phenylalkyl of 7 to 10 carbon atoms,
$R_3$ is hydrogen or alkyl of 1 to 4 carbon atoms,
and $R_4$ is hydrogen or alkyl of 1 to 4 carbon atoms.

The invention also provides a process for the production of the compounds of formula I, comprising, a) producing a compound of formula I$a$,

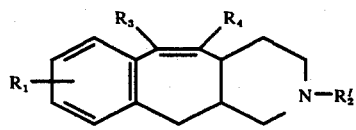

wherein
$R_1$, $R_3$ and $R_4$ are as defined above, and
$R_2{}^I$ is hydrogen, alkyl of 1 to 4 carbon atoms or cycloalkylalkyl of 5 to 10 carbon atoms, the cycloalkyl radical thereof containing at least four carbon atoms, phenylalkyl of 7 to 10 carbon atoms, and, when $R_3$ is hydrogen, also alkenyl or alkinyl each of 3 to 6 carbon atoms, the multiple bond thereof being other than adjacent to the nitrogen atom of the tricyclic ring system, or cyclopropylalkyl of 4 to 7 carbon atoms,
by removing water from a compound of formula II,

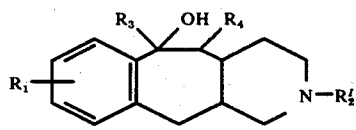

wherein $R_1$, $R_2{}^I$, $R_3$ and $R_4$ are as defined above, or b) producing a compound of formula I$b$,

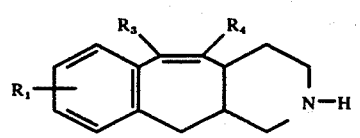

wherein $R_1$, $R_3$ and $R^4$ are as defined above, by splitting off the radical $R_5$, and in case A is hydroxyl and B is hydrogen, also splitting off water from a compound of formula III,

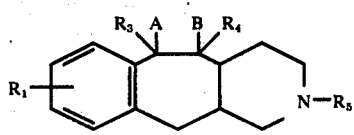

wherein
$R_1$, $R_3$ and $R_4$ are as defined above,
either
A and B together signify a bond
or
A is OH and B is H provided that when $R_3$ is other than hydrogen, A and B signify a bond,
and
$R_5$ is a radical removable by solvolysis, said radical being removable by solvolysis in the presence of acid when A is OH and B is H,
the solvolysis being carried out in the presence of an acid when A is OH and B is H, or c) producing a compound of formula I$c$,

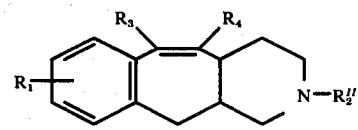

wherein
$R_1$, $R_3$ and $R_4$ are as defined above, and
$R_2{}^{II}$ is alkyl of 1 to 4 carbon atoms or cycloalkylalkyl of 5 to 10 carbon atoms, the cycloalkyl ring thereof containing at least four carbon atoms, alkenyl or alkinyl of 3 to 6 carbon atoms, the multiple bond thereof being other than adjacent to the nitrogen atom of the tricyclic ring structure, oxoalkyl of 2 to 5 carbon atoms, the oxygen atom thereof being separated by at least two carbon atoms from the nitrogen atom of the tricyclic ring system, or phenylalkyl of 7 to 10 carbon atoms,
by alkylating a compound of formula I$b$, or d) producing a compound of formula I$d$,

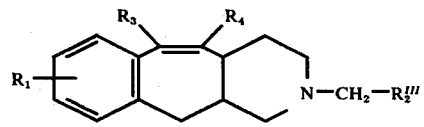

wherein
$R_1$, $R_3$ and $R_4$ are as defined above, and
$R_2{}^{III}$ is hydrogen, alkyl of 1 to 3 carbon atoms, cycloalkylalkyl of 4 to 9 carbon atoms, cycloalkyl of 3 to 6 carbon atoms, phenylalkyl of 7 to 9 carbon atoms, or phenyl
by reducing a compound of formula IV,

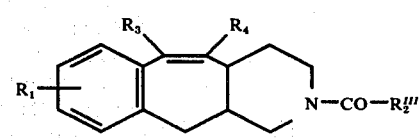

wherein $R_1$, $R_2{}^{III}$, $R_3$ and $R_4$ are as defined above.

In the compounds of formula I the substituent $R_1$ preferably signifies hydrogen. When $R_1$ is halogen, this preferably is chlorine. When $R_1$ is alkyl as defined above, this especially signifies methyl.

The substituent $R_2$ preferably signifies hydrogen or alkyl as defined above, especially methyl or ethyl. When $R_2$ is alkenyl or alkinyl as defined above, these groups preferably contain 3 or 4 carbon atoms. When $R_2$ is oxoalkyl as defined above, the oxygen atom is preferably separated by 2 or 3 carbon atoms from the nitrogen atom. When $R_2$ is phenylalkyl as defined above, this especially signifies phenethyl. When $R_2$ is cycloalkylalkyl as defined above, the alkylene chain thereof contains from 1 to 4, preferably 1 or 2 carbon atoms, and the cycloalkyl ring contains 3 to 6, preferably 3 or 4 carbon atoms.

The substituent $R_3$ preferably signifies alkyl as defined above and especially signifies methyl.

The substituent $R_4$ preferably signifies hydrogen. When $R_4$ is alkyl as defined above, this especially signifies methyl.

The rings B and C in the compounds of formula I are preferably joined by a trans linkage.

The preferred compounds of formula I are those wherein $R_1$ is hydrogen, $R_2$ is hydrogen or alkyl as defined above, especially methyl, $R_3$ is alkyl as defined above, especially methyl, $R_4$ is hydrogen, and the rings B and C are joined by a trans linkage.

A further group of the compounds of formula I, is that in which $R_1$ and $R_3$ are as defined above, $R_2$ signifies hydrogen, alkyl of 1 to 4 carbon atoms, cycloalkylalkyl of 4 to 10 carbon atoms, alkenyl or alkinyl of 3 to 6 carbon atoms, the multiple bond thereof being other than adjacent to the nitrogen atom of the tricyclic ring system, oxoalkyl of 2 to 5 carbon atoms, the oxygen atom thereof being separated by at least two carbon atoms from the nitrogen atom of the tricyclic ring system or benzyl, and $R_4$ is hydrogen.

Process variant a) may be effected in known manner. For example, a compound of formula II may be reacted with a suitable water-removing agent. The reaction may be effected in the presence of an inert organic solvent. Suitable water-removing agents, which may be used, are strong acids or acid anhydrides thereto, or acid halides. When $R_2{}'$ in the compounds of formula II is an alkenyl or alkinyl group, the reaction is preferably effected in the presence of acid anhydrides or halides, e.g. acetic anhydride or thionyl chloride. The reaction may suitably be effected at a temperature of from 0° to 100° C.

The removal of the radical $R_5$ from compounds of formula III, according to process variant b) may be effected solvolytically, especially hydrolytically, employing conventional methods for the removal of amino-protective groups from heterocyclic amines. Suitable protective groups for a heterocyclic amino group, capable of being removed solvolytically, especially hydrolytically are, for example, acyl groups, preferably alkoxy- or arylcarbonyl groups, especially lower alkyloxycarbonyl groups such as ethoxycarbonyl, or the nitrile group. The removal of the radical $R_5$ may be effected either in an acid medium, suitably in the presence of a strong mineral acid, or in an alkaline medium, for example in the presence of an inorganic base, the preferred medium depending on the nature of the radical $R_5$. When $R_5$ signifies alkoxy- or aryloxycarbonyl, the process may conveniently be effected solvolytically, employing conventional techniques for urethane splitting, for example with a lower alcohol, such as ethanol or n-butanol, or with water, suitably in the presence of an inert organic solvent which, preferably, is miscible with water, for example in the presence of an aqueous or alcoholic alkali metal hydroxide solution or, alternatively, in the presence of a mineral acid, for example a hydrohalic acid or sulphuric acid, which may, if desired, be diluted with water. The reaction may suitably be effected at a temperature of from 20° to 150° C. When $R_5$ signifies nitrile, the process may conveniently be effected hydrolytically according to conventional methods for the hydrolysis of cyanamides, preferably in the presence of a strong mineral acid.

When A is hydroxyl and B is hydrogen, the process may conveniently be effected in the presence of a strong acid to effect simultaneous removal of water.

The alkylation of compounds of formula Ib in accordance with process variant c) may be effected in accordance with conventional methods for aminoalkylation. By alkylation is meant, the substitution of the nitrogen atom of the tricyclic system of compounds Ib, with an alkyl, cycloalkylalkyl, alkenyl, alkinyl, oxoalkyl or phenylalkyl radical as defined in relation to substituent $R_2{}''$. For example, a compound of formula Ib may be reacted in known manner with a compound of formula V, $$X - R_2{}'' \qquad \qquad V$$

wherein $R_2{}''$ is as defined above, and

X is the acid radical of a reactive ester, preferably halogen or an organic sulphonic acid radical.

The reaction is preferably effected in an inert organic solvent at a temperature of from 20° C to the reflux temperature of the reaction mixture. The reaction is preferably effected in the presence of a basic condensation agent, for example an organic amine or an alkali metal carbonate, or in the presence of an excess of a compound of formula Ib.

Process variant d) may be effected in accordance with conventional methods for the reduction of amides to amines. For example, the reduction may be effected with complex metal hydrides in an inert solvent. Suitable complex metal hydrides are, for example, complex aluminium hydrides, preferably lithium aluminium hydride.

The resulting compounds of formula I may be isolated and purified using conventional techniques. Where required, free base forms of the compounds may be converted into acid addition salt forms, and vice versa, in conventional manner.

The compounds of formula I may exist as cis and trans isomers with respect to the 4a, 11a ring junction. Since the configuration at this ring junction is maintained, the stereochemistry of the final product at this junction is the same as that of the starting materials. Where an isomeric mixture of starting materials is employed, the final product comprises a mixture of cis and trans isomers which may, if desired, be separated by conventional techniques.

The starting materials may be obtained as follows:

a'. A compound of formula IIa,

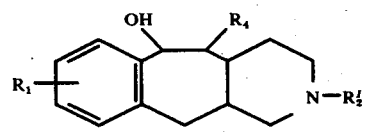

wherein $R_1$, $R_2^I$ and $R_4$ are as defined above, may, for example, be obtained by reducing a compound of formula VI,

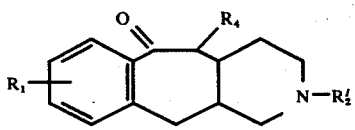

wherein $R_1$, $R_2^I$ and $R_4$ are as defined above. The reduction may, for example, be effected with lithium aluminium hydride or sodium borohydride, or, when $R_2^I$ is other than an alkenyl or alkinyl group, also by catalytic hydrogenation. When $R_2^I$ is benzyl, the benzyl group is likewise split off during catalytic hydrogenation.

b'. A compound of formula IIb,

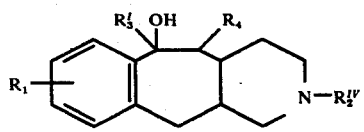

wherein
$R_1$ and $R_4$ are as defined above, and
$R_2^{IV}$ is alkyl, cycloalkylalkyl or phenylalkyl as defined above for the substituent $R_2^I$, and
$R_3^I$ is alkyl of 1 to 4 carbon atoms, may, for example, be obtained by reacting a compound of formula VIa,

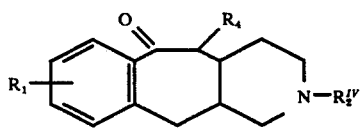

wherein $R_1$, $R_2^{IV}$ and $R_4$ are as defined above, with a compound of formula VIIa, $$R_3^I\text{-Mg-}X^I \qquad \text{VIIa}$$

or VIIb, $$R_3^I\text{-Li} \qquad \text{VIIb}$$

wherein
$R_3^I$ is as defined above, and
$X^I$ is chlorine, bromine or iodine.

c'. A compound of formula IIc,

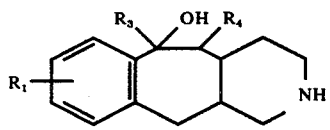

wherein $R_1$, $R_3$ and $R_4$ are as defined above, may, for example, be obtained by hydrogenolytic debenzylation of the corresponding N-benzyl compound.

d'. A compound of formula VIb,

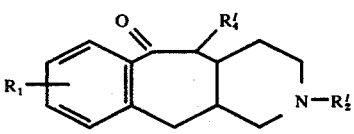

wherein
$R_1$ and $R_2^I$ are as defined above, and
$R_4^I$ is alkyl of 1 to 4 carbon atoms, may, for example, be obtained by alkylating a compound of formula VIc,

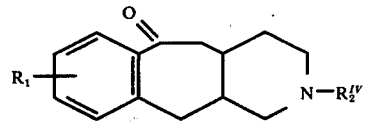

wherein $R_1$ and $R_2^{IV}$ are as defined above, with preferably an equivalent amount of an alkyl halide, in the presence of a strong base, for example potassium t-butylate, to obtain the corresponding compound wherein $R_2^I$ is $R_2^{IV}$ and compounds of formula VIb, in which $R_2^I$ is other than $R_2^{IV}$, may be prepared from the N-methyl compound by converting this compound to the NH compound and, thereafter, introducing the desired alkyl group by alkylation in known manner.

e'. A compound of formula VId,

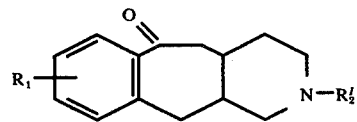

wherein $R_1$ and $R_2^I$ are as defined above, may, for example, be obtained by removing the alkoxycarbonyl group in accordance with the usual methods for urethane splitting, from a compound of formula VIe,

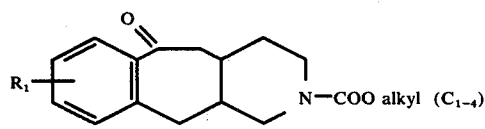

wherein $R_1$ is as defined above, and introducing any further desired radicals $R_2^I$ into the resulting NH compound by alkylation.

f'. Compounds of formulae VIc and VIe may, for example, be obtained by cyclizing a compound of formula VIII,

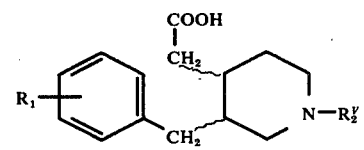

wherein
$R_1$ is as defined above, and
$R_2^V$ is as defined above for $R_2^{IV}$, or an alkoxycarbonyl group, or a reactive acid derivative thereof, for example an acid halide, or ester, preferably in the presence of polyphosphoric acid.

g'. A compound of formula VIIIa,

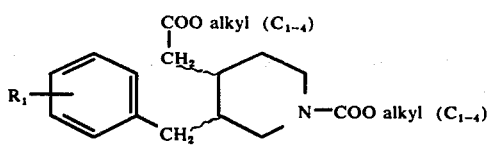

VIIIa wherein $R_1$ is as defined above, may, for example, be obtained from a compound of formula IX,

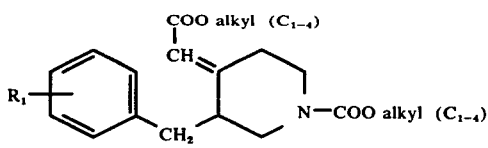

IX wherein $R_1$ is as defined above, by catalytic hydrogenation, preferably in the presence of a platinum oxide or palladium catalyst. This hydrogenation yields mixtures of isomers of the compounds of formula VIIIa wherein the substituents in the 3 and 4 positions of the piperidine ring are either in a cis or trans position one to another.

h'. The remaining compounds of formula VIII may be obtained from compounds of formula VIIIa by hydrolysis of the latter compounds, by boiling for several hours in concentrated hydrochloric acid, and thereafter, alkylating the resulting 3-benzyl-4-piperidine acetic acid in accordance with conventional methods for aminoalkylation, to introduce the radical $R_2^V$. Any resulting esters of the acids of formula VIII are thereafter hydrolysed.

i'. A compound of formula IX may, for example, be obtained by reacting a piperidine of formula X,

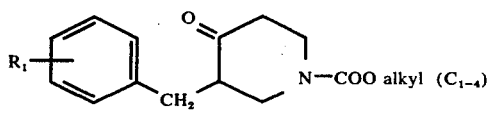

X wherein $R_1$ is as defined above, with a phosphonodiethyl acetate of formula XI.

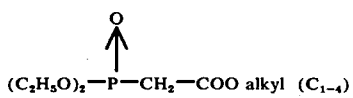

XI

The reaction is preferably effected in the presence of a basic condensation agent, for example, an alkali meal alcoholate.

j'. A compound of formula III wherein $R_5$ is alkyloxyor aryloxycarbonyl or nitrile, may be obtained from the corresponding N-methyl compound in known manner by reaction with a suitable chloroformic acid ester or with cyanogen bromide. Other compounds of formula III may be produced in conventional manner.

k'. A compound of formula IV may be obtained by acylation of the corresponding compound of formula Ib, for example by reacting the compound of formula Ib with an acid chloride of formula XII,

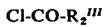   XII wherein $R_2^{III}$ is as defined above.

The compounds of formula VIII and VIIIa can exist as cis and trans isomers. If desired, the isomers may be separated following their production or, alternatively the isomer mixture may be used, in which case, the isomeric product mixtures arising therefrom may be separated after the completion of any stage (including the last stage to produce compounds I) in the reaction sequence. The separation of the isomers may be effected in conventional manner.

Insofar as the production of the starting materials is not described, these are known or may be produced in accordance with known processes, or in a manner analogous to the processes described herein or to known processes.

The compounds of formula I possess pharmacological activity. In particular, the compounds exhibit antidepressant activity as indicated in standard tests in animals, for example in the following tests:

The compounds are useful because they possess pharmacological activity in animals. In particular the compounds exhibit antidepressant activity as indicatd in standard tests in animals, for example the following tests:-

1. In one standard test in accordance with the method of G. Stille [Arz. Forsch 14, 534–7 (1964)] an antagonism of the ptosis and catalepsy induced in rats by tetrabenazine is observed. The compounds are administered i.p. at from about 10 to about 100 mg/kg animal body weight. The tetrabenazine is administered i.p. 30 minutes after the administration of the compounds at a dosage of 10 mg/kg animal body weight.

2. In another standard test in accordance with the method of Anton A. H., Sayre, D. F.: A study of the factors affecting the aluminium oxide-trihydroxyindole procedure for the analysis of catecholamines. J.Pharmac. exp. Therap. 138 360–375 (1962), an inhibition of the uptake of exogenous noradrenaline by rat brain tissue is observed. In this test $^3$H-noradrenaline is injected stereotaxically into the lateral ventricles of the rat brain. After homogenization the unmetabolised 3H-noradrenaline and its deaminated metabolites are separated from methylated noradrenaline metabolites in conventional manner using aliminium oxide. The percent change of unmetabolised and deaminated $^3$H-noradrenaline between control rats and those pretreated with 40 mg/kg animal body weight of the test substance is observed. The inhibition of noraldrenaline up-take is determined from the decrease of the unmetabolised and deaminated noradrenaline metabolites and the simultaneous increase in the amount of methylated noradrenaline metabolites.

3. In a further test in accordance with the method of Gillespie and Muir (Brit. J. Pharmacol, 1967 30, 78 and 1970 40, 257), the compounds potentiate the noradrenaline-induced pressor response in the pithed rat. The noradrenaline is administered i.v. at a dosage of 1 microgram per rat. The increased blood pressure in the carotid artery is recorded.

In this test the compounds are administered i.v. at from about 0.01 to about 0.5 mg/kg animal body weight.

4. In a further standard test based on the method of Spencer. P.S.J. (1965) Brit. J. Pharmacol. 25 442 an antagonism of oxotremorine-induced tremors and hypothermia is observed. In this test mice are acclimatised to laboratory conditions overnight. 2 mg/kg animal body weight of atropine methyl nitrate is administered s.c.; 10 minutes later the test substance is administered. 20 Minutes later rectal temperatures are measured with a probe. The presence of tremors is also assessed. Oxotremorine at a dose of 0.5 mg/kg animal body weight is then administered s.c. The hypothermia and inhibition of tremors is then determined.

The compounds of formula I are therefore useful as anti-depressants for the treatment of endogenous and exogenous depressions.

For this use the dosage will, of course, vary depending on the compound employed, mode of administration and treatment desired. However, in general, satisfactory results are obtained when administered at a daily dosage of from about 0.01 mg to about 100 mg per kg animal body weight, conveniently given in divided doses 2 to 4 times a day or in sustained release form. For the larger mammals, the total daily dosage is in the range from about 5 to about 500 mg, and dosage froms suitable for oral administration comprise from about 1.5 mg to about 250 mg of the compounds admixed with a solid or liquid pharmaceutical carrier or diluent.

In one example the compounds may be administered at from about 1 to about 100 mg/kg animal body weight per day. For larger mammals the daily dose may be from about 50 to about 500 mg.

A particularly preferred compound of formula I is trans-2,3,4,4a,11,11a-hexahydro-2,6-dimethyl-1H-benzo[5,6] cyclohepta[1,2-c]pyridine.

In the following Examples all temperatures are in degress Centigrade and are uncorrected.

EXAMPLE 1

Trans-2,3,4,4a,11,11a-hexahydro-2-methyl-1H-benzo[5,6]cyclohepta[1,2-c]pyridine [Process variant a)]

a. 1-ethoxycarbonyl-3-benzyl-4-piperidylene-acetic acid ethyl ester [Compound IX]

67g of potassium t-butylate are added portionwise to a solution of 136 g of phosphonoacetic acid triethyl ester in 125 cc of dimethyl formamide while cooling with ice. The reaction mixture is stirred at room temperature for 1 hour, and a solution of 105 g of 3-benzyl-4-oxo-1-piperidinecarboxylic acid ethyl ester in 90 cc of absolute toluene is added dropwise at such a rate that the internal temperature does not exceed 35°. After the dropwise addition the reaction mixture is stirred at 70° for 18 hours, is cooled to 0°–10°, and 400 cc of 2.5 N hydrochloric acid are added dropwise. After diluting with 800 cc of benzene, the mixture is stirred for a further 30 minutes, the organic phase separated, washed with a 10% potassium carbonate solution and then with water, dried over sodium sulphate and concentrated by evaporation. The residue is distilled in a high vacuum, whereby 1-ethoxy-carbonyl-3-benzyl-4-piperidylidene-acetic acid ethyl ester distils at 160°–165°/0.005 mm Hg.

b. 1-ethoxycarbonyl-3-benzyl-4-piperidine-acetic acid ethyl ester [Compound VIIIa - isomer mixture]

A solution of 114 g of 1-ethoxycarbonyl-3-benzyl-4-piperidylidene-acetic acid ethyl ester in 120 cc of ethyl acetate is hydrogenated in the presence of 15 g of 10% palladium on charcoal at 11 atmospheres and at a temperature of 50° for 18 hours. After removing the catalyst, the solvent is evaporated at reduced pressure. The 1-ethoxycarbonyl-3-benzyl-4-piperidine-acetic acid ethyl ester (mixture of isomers) obtained as residue, is used for the next reaction step without purification.

c. 3-benzyl-1-methyl-4-piperidine-acetic acid ethyl ester [Compound VI - isomer mixture]

A mixture of 114 g of 1-ethoxycarbonyl-3-benzyl-4-piperidine-acetetic acid ethyl ester and 2 liters of concentrated hydrochloric acid is heated to the boil while stirring for 24 hours. The resulting solution is then evaporated to dryness and dried in a high vacuum at 100° for 2 to 3 hours. The resulting crude 3-benzyl-4-piperidine-acetic acid hydrochloride (mixture of isomers) is used for the next reaction step. The crude product may be recrystallized from acetone, whereby the α-isomer, having an M.P. of 178°–179°, is obtained.

A mixture of 95 g of 3-benzyl-4-piperidine-acetic acid hydrochloride (mixture of isomers), 30 cc of concentrated ammonia solution, 900 cc of a 33% formaldehyde solution and 140 cc of 90% formic acid is heated to the boil for 18 hours. After cooling to room temperature and adding 120 cc of concentrated hydrochloric acid, the mixture is evaporated to dryness at reduced pressure and the residue is dried at 100° in a high vacuum for 5 hours. The resulting crude 3-benzyl-1-methyl-4-piperidine-acetic acid hydrochloride (mixture of isomers) is used for the next reaction without purification.

The crude hydrochloride obtained above is dissolved in 2.5 liters of absolute ethanol, 12 cc of concentrated sulphuric acid are added, the mixture is heated to the boil for 24 hours, a further 12 cc of concentrated sulphuric acid are added, and heating to the boil is again effected for 24 hours. The reaction mixture is concentrated to about 500 cc at reduced pressure, diluted with 2 liters of ice/water, washed out with ether and made alkaline with concentrated caustic soda solution. The oil which separates is extracted with ether, the extracts are washed with water, dried over sodium sulphate and concentrated by evaporation. The residue is distilled in a high vacuum, whereby 3-benzyl-1-methyl-4-piperidine-acetic acid ethyl ester (mixture of isomers) distils at 120°–125°/0.02 mm Hg.

d. 1,2,3,4,4a,5,11,11a-octahydro-2-methyl-6H-benzo[5,6]-cyclohepta[1,2-c]pyridin-6-one [Compound V isomer mixture]

27 g of 3-benzyl-1-methyl-4-piperidine-acetic acid ethyl ester are slowly added to 250 g of polyphosphoric acid previously heated to 100°, the temperature is raised to 130° and the reaction mixture is stirred at this temperature for 2 hours. After cooling to room temperature the reaction mixture is poured on 1 liter of water, the resulting solution is washed out with ether and made alkaline with potassium carbonate (pH 9 to 10). The 1,2,3,4,4a5,11,11a-octahydro-2-methyl-6H-benzo[5,6]-cyclohepta[1,2-c]pyridin-6-one which separates as an oil, is extracted with ether, the extracts are washed with water, dried over sodium sulphate, concentrated by evaporation and distilled in a high vacuum. The mixture of isomers has a B.P. of 135°–140°10.05 mm Hg.

Separation of isomers: A solution of 48 g of fumaric acid in 1000 cc of ethanol is added to a solution of 95 g of the mixture of isomers in 300 cc of ethanol and the mixture is allowed to stand at room temperature for 48 hours, whereby trans-1,2,3,4,4a,5,11,11a-octahydro-2-methyl-6H-benzo[5,6]cyclohepta[1,2-b]-paridin-6-one hydrogen fumarate crystallizes. M.P. 201°–202° (after recrystallization from ethanol).

The mother liquor obtained from the first crystallization is evaporated to dryness. Water and methylene chloride are added to the residue and the mixture is made alkaline by the addition of caustic soda solution. After separating the organic solution, the aqueous phase is again extracted thrice with methylene chloride, the combined organic solutions are washed with water, dried over potassium carbonate and concentrated by evaporation. The residue is dissolved in isopropanol and converted into the hydrochloride with hydrochloric acid in ether. After standing at 0° for several hours, the hydrochloride of cis-1,2,3,4,4a,5,11,11a-octahydro-2-methyl-6H-benzo[5,6-cyclohepta[1,2-i c]pyridin-6-one is filtered off and recrystallized from isopropanol. M.P. 241°–243°.

e.
Trans-2,3,4,4a5,6,11,11a-octahydro-2-methyl-1H-benzo[5,6]cyclohepta[1,2-c]pyridin-6-ol [Compound II]

A solution of 10.0 g of trans-1,2,3,4,4a5,11,11a-octahydro-2-methyl-6H-benzo[5,6]cyclohepta[1,2-c]-pyridin-6-one in 200 cc of anhydrous ether is added dropwise at room temperature to a suspension of 8.0 g of lithium aluminium hydride in 550 cc of anhydrous ether, the reaction mixture is stirred at the same temperature for 1 hour, and 150 cc of ethyl acetate are added dropwise at 0°–10°. After the dropwise addition of 80 cc of water the inorganic residue is filtered off, washed out with ether, the separated water is removed from the filtrate and the ethereal solution is dried over magnesium sulphate. After removing the solvent by evaporation, the resulting trans-2,3,4,44,5,6,11,11a-octahydro-2-methyl-1H-benzo[5,6]cyclohepta[1,2-c]pyridin-6-ol may be recrystallized from acetone. M.P. 193°–194°.

f.
Trans-2,3,4,4a,11,11a-hexahydro-2-methyl-1H-benzo[5,6-cyclohepta[1,2-c]pyridine [Compound Ia]

A solution of 12.0 g of trans-2,3,4,4a,5,6,11,11a-octahydro-2-methyl-1H-benzo[5,6]-cyclohepta[1,2c-]pyridin-6-ol in 30 cc of concentrated hydrochloric acid and 30 cc of water, is boiled at reflux for 15 minutes, cooled, diluted with 200 cc of water and made alkaline (pH 14) with a 20% caustic soda solution. The oil which separates is extracted with methylene chloride, the organic phase is washed with water until neutral, dried over sodium sulphate and concentrated by evaporation. The oily residue is dissolved in 20 cc of ethanol. A solution of 6.0 g of fumaric acid in 40 cc of ethanol is then added, and the hydrogen fumarate of the title compound, which crystallizes, is filtered after cooling and recrystallized from ethanol. M.P. 215°–216°C.

EXAMPLE 2

Cis-2,3,4,4a11,11a-hexahydro-2-methyl-1H-benzo[5,6]cyclohepta[1,2-c]pyridine [Process variant a)]

The title compound is produced in a manner analogous to that described in Example 1, from 8.5 g of cis-2,3,4,4a,5,6,11,11a-octahydro-2-methyl-1H-benzo[5,6]cyclohepta[1,2-c]pyridin-6-ol (produced in a manner analogous to Example 1 g) by reduction of cis-1,2,3,4,4a,5,11,11a-octahydro-2-methyl-6H-benzo[5,6]cyclohepta[1,2-c]pyridin-6-one, M.P. 140°–144°), 26 cc of concentrated hydrochloric acid and 26 cc of water; the title compound is isolated as hydrogen fumarate. M.P. 116°–120° (from ethanol/ether).

EXAMPLE 3

Trans-2,3,4,4a11,11a-hexahydro-2,6-dimethyl-1H-benzo[5,6]cyclohepta[1,2-c]pyridine [Process variant a)]

a.
Trans-2,3,4,4a,5,6,11,11a-octahydro-2,6-dimethyl-1H-benzo[5,6cyclohepta[1,2-c]pyridin-6-ol [Compound II]

A solution of 13.0 g of trans-1,2,3,4,4a,5,11,11a-octahydro-2-methyl-6H-benzo[5,6]cyclohepta[1,2-c]pyridin-6-one in 250 cc of anhydrous benzene is added dropwise at room temperature within 1 hour to a solution of 73 cc of 2 M methyl lithium in ether and 250 cc of anhydrous ether. The reaction mixture is stirred at room temperature for 5 hours, is poured on 700 cc of a 20% ammonium chloride solution, the organic solution is separated and the aqueous phase is extracted with methylene chloride. The combined organic solutions are washed with water, dried over sodium sulphate and concentrated by evaporation, and the resulting trans-2,3,4,4a,5,6,11,11a-octahydro-2,6-dimethyl-1H-benzo[5,6]cyclohepta[1,2-c]pyridin-6-ol is used as such for the next reaction.

b.
Trans-2,3,4,4a,11,11a-hexahydro-2,6-dimethyl-1H-benzo-[5,6]cyclohepta[1,2-c]pyridine 12.5 g of trans-2,3,4,4a,5,6,11,11a-octahydro-2,6-dimethyl-1H-benzo[5,6]cyclohepta[1,2-c]pyridin-6-ol are heated to the boil in 180 cc of concentrated hydrochloric acid and 120 cc of water for 15 minutes, the mixture is evaporated to dryness at reduced pressure, and the hydrochloride of the title compound, obtained as solid residue, is recrystallised twice from acetone. M.P. 234°–236°C.

EXAMPLE 4

Trans, 2,3,4,4a11,11a-hexahydro-2,5,6-trimethyl-1H-benzo[5,6]cyclohepta-[1,2-c]pyridine a.
Trans-2,3,4,4a,5,6,11,11a-octahydro-2,5-dimethyl-6H-benzo[5,6]cyclohepta[1,2-c]pyridin-6-one [Compound VI]

5.9 g of potassium tert.butylate are slowly added with stirring to a solution previously heated to 50° of 10.0 g of trans-1,2,3,4,4a5,11,11a-octahydro-2-methyl-6H-benzo[5,6]cyclohepta[1,2-c]pyridin-6-one in 300 cc of cyclohexane. The reaction mixture is stirred at the same temperature for 15 minutes, is cooled to 20°, 7.2 g of methyl iodide are added dropwise and stirring is subsequently effected for a further 4 hours at room temperature. After the addition of 300 cc of water and 200 cc of benzene, the organic solution is separated, washed with water, dried over sodium sulphate and concentrated by evaporation. The resulting trans-1,2,3,4,4a,5,11,11a-octahydro-2,5-dimethyl-6H-benzo[5,6]cyclohepta[1,2-c]pyridin-6-one, obtained as residue, is recrystallized twice from ether/hexane. M.P. 101°–102°.

b.
Trans-2,3,4a,5,6,11,11a-octahydro-2,5,6-trimethyl-1H-benzo[5,6]cycloheptal[1,2-c]pyridin-6-ol [Compound II]

b.   Trans-2,3,4,4a,5,6,11,11a-octahydro-2,5,6-trimethyl-1H-benzo[5,6]cyclohepta[1,2-c]pyridin-6ol is produced in a manner analogous to that described in Example 3a), from 6.5 g of the above product in 120 cc of anhydrous benzene and 34.5 cc of 2 M methyl lithium in ether and 120 cc of anhydrous ether, and is used in crude state for the next reaction.

c.
Trans-2,3,4,4a-11,11a-hexahydro-2,5,6-trimethyl-1H-benzo[5,6]cyclohepta[1,2-c]pyridine 7.0 g of trans-2,3,4,4a,5,6,11,11a-octahydro-2,5,6-trimethyl-1H-benzo[5,6]cyclohepta[1,2-c]pyridine-6-ol are heated to the boil in 100 cc of concentrated hydrochloric acid and 70 cc of water for 30 minutes, the reaction mixture is cooled to 10°, is worked up in a manner analogous to that described in Example 1, and the title compound obtained as an oil is converted into the hydrogen fumarate and recrystallised. M.P. 184°–185° (from isopropanol). The following 2,3,4,4a,11,11a-hexahydro-1H-benzo[5,6]cyclohepta[1,2-c]pyridine derivatives may also be obtained in a manner analogous to that described in Examples 1 to 4, by the removal of water from the corresponding 2,3,4,4a,5,6,11,11a-octahydro-1H-benzo[5,6]cyclohepta[1,2-c]pyridin-6-ols:

hexahydro-2,6-dimethyl-1H-benzo[5,6]cyclohepta[1,2-c]pyridine with chlorofornic acid ethyl ester), and the mixture is heated to the boil for 1½ hours. After cooling to room temperature the reaction mixture is poured on 1 liter of water, is made alkaline (pH 14) with concentrated caustic soda solution, and the precipitated product is extracted with benzene. The benzene solutions are washed with water, dried over sodium sulphate and concentrated by evaporation. The title compound obtained as an oil is converted into its hydrochloride in acetone. M.P. 233°–234° (recrystallized twice from isopropanol/acetone).

The compounds indicated in Example 4 B, 4 D and 4 I may also be obtained in a manner analogous to that described in Example 5 by removing the amino-protective group from the corresponding compounds of formula III.

EXAMPLE 6

Trans-2,3,4,4a,11,11a-hexahydro-1H-benzo[5,6]cyclohepta[1,2-c]pyridine-2-propan-2-one

[Process variant Ic)]

A solution of 3.6 g of chloroacetone in 20 cc of N,N-dimethyl formamide is added dropwise at 70° within 30 minutes to a mixture of 9.0 g of trans-2,3,4,4a,11,11a-hexahydro-1H-benzo[5,6]cyclohepta[1,2-c]pyridine hydrochloride and 8.1 g of sodium carbonate in 50 cc of N,N-dimethyl formamide, the reaction mixture is stirred at the same temperature for 2 hours, is cooled to room temperature and poured on 300 cc of ice water. The aqueous suspension is extracted with methylene

| Example No. | $R_1$ | $R_2$ | $R_3$ | $R_4$ | Structure | M.P. |
|---|---|---|---|---|---|---|
| 4 A | H | —$CH_3$ | —$CH_3$ | H | cis | HCl*: 284–285° |
| 4 B | H | H | H | H | trans | HCl*: 246–247° |
| 4 C | H | H | —$CH_3$ | H | trans | HCl*: 233–234° |
| 4 D | H | H | —$CH_3$ | H | cis | HCl*: Z** from 255° |
| 4 E | H | —$C_2H_5$ | —$CH_3$ | H | trans | hfu***: 189–190° |
| 4 F | H | —CH(CH$_3$)$_2$ | —$CH_3$ | H | trans | hfu***: 220–221° |
| 4 G | H | —$CH_3$ | H | —$CH_3$ | trans | hfu***: 215–216° |
| 4 H | H | —$CH_3$ | H | —$CH_3$ | cis | HCl* : Z** from 262° |
| 4 I | 8-$CH_3$ | H | H | H | trans | hfu***: 184–186° |
| 4 J | 8-Cl | —$CH_3$ | H | H | trans | hfu***: Z** from 184° |
| 4 K | 8-Cl | —$CH_3$ | —$CH_3$ | H | trans | hfu***: Z** from 206° |
| 4 L | H |  | —$CH_3$ | H | trans | |
| 4 M | H |  | H | H | trans | |
| 4 N | H |  | —$CH_3$ | H | trans | hml****: 174–175° |

* HCl = hydrochloride
** Z = decomposition
*** hfu = hydrogen fumarate
**** hml = hydrogen maleate

EXAMPLE 5

Trans-2,3,4,4a,11,11a-hexahydro-6-methyl-1H-benzo[5,6]cyclohepta[1,2-c]1,2-c]pyridine

[Process variant Ib)]

110 cc of glacial acetic acid and 110 cc of 48% hydrobromic acid are added to 11.0 g of trans-2,3,4,4a,11,11a-hexahydro-6-methyl-1H-benzo[5,6-]cyclohepta[1,2-c]pyridine-2-carboxylic acid ethyl ester (obtained by reaction of trans-2,3,4,4a,11,11a- chloride, the extract is washed with water, dried over potassium carbonate and concentrated by evaporation. The title compound obtained as an oil is converted into the hydrogen maleate in ethanol/ether. M.P. 132°–133° (recrystallized twice from ethanol/ether).

The compounds indicated in Examples 1, 2, 3, 4, 4 A, 4 E, 4 F, 4 G, 4 H, 4 J, 4 K, 4 L, 4 M and 4 N and the following compound may also be obtained in a manner analogous to that described in Example 6 by alkylation of the corresponding NH compounds:

| Example Nr. | Structure | R₁ | R₂ | R₃ | R₄ | M.P. |
|---|---|---|---|---|---|---|
| 6 A | trans | H | —CH₂—C≡CH | CH₃ | H | hml* 164–165° |

*hml = hydrogen maleate

EXAMPLE 7

Trans-2-cyclopropylmethyl-2,3,4,4a,11,11a-hexahydro-1H-benzo[5,6]cyclohepta[1,2-c]pyridine [Process variant Id)]

A solution of 10.0 g of trans-2-cyclopropylcarbonyl-2,3,4,4a,11,11a-hexahydro-1H-benzo[5,6]cyclohepta[1,2-c]pyridine (obtained by reaction of trans-2,3,4,4a,11,11a-hexahydro-1H-benzo[5,6]cyclohepta[1,2-c]-pyridine with cyclopropanecarboxylic acid chloride) in 150 cc of anhydrous tetrahydrofuran is added dropwise, while stirring, at 10°–15°, to a solution of 2.5 g of lithium aluminium hydride in 350 cc of anhydrous tetrahydrofuran, and the reaction mixture is stirred at room temperature for 2 hours. The reaction mixture is decomposed at 0°–5° by the dropwise addition of 12 cc of saturated sodium sulphate solution, the inorganic portion is filtered off and washed out with methylene chloride. The combined filtrates are dried over sodium sulphate, concentrated by evaporation, and the title compound obtained as oily residue is converted into the hydrogen fumarate in isopropanol/acetone and is recrystallized. M.P. 157°–159°.

The compounds indicated in Examples 1, 2, 3, 4, 4 A, 4 E, 4 G, 4 H, 4 J, 4 K, 4 L, 4 M and 4 N may also be obtained in a manner analogous to that described in Example 7, by reduction of the corresponding acyl compounds.

The compounds of formula I may be administered in pharmaceutically acceptable acid addition salt form. Such acid addition salt forms exhibit the same order of activity as the free base forms and are readily prepared in conventional manner. Representative acid addition salt forms include organic acid salt forms such as the hydrogen maleate, fumarate, tartrate and methane sulphonate and mineral acid salt forms such as the hydrochloride, hydrobromide and sulphate. A pharmaceutical composition may comprise a compound of formula I, in free base form or in pharmaceutically acceptable acid addition salt form, in association with a pharmaceutical carrier or diluent. Such compositions conveniently contain more than 1% by weight of the compound of formula I and may be prepared by conventional techniques to be in conventional forms, for example, capsules, tablets, suppositories, dispersible powders, syrups, elixirs, suspensions or solutions, for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethyelne stearate and polyoxyethylene sorbitan monooleate, granulating and disintegrating agents such as starch and alginic acid, binding agents such as starch, gelatin and acacia, and lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastrointestinal track and thereby provide sustained action over a long period.

The preferred compositions from the standpoint of ease of administration are solid compositions, particularly solid-filled gelatin capsules and tablets.

In a group of compounds R₂ when phenylalkyl is benzyl. In a further group R₄ is hydrogen.

I claim:

1. A compound of formula I,

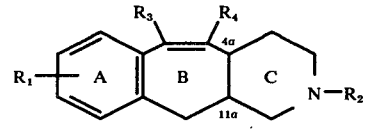

wherein

R₁ is a hydrogen, alkyl of 1 to 4 carbon atoms, fluorine, chlorine or bromine,

R₂ is hydrogen, alkyl of 1 to 4 carbon atoms, cycloalkylalkyl of 4 to 10 carbon atoms, alkenyl of 3 to 6 carbon atoms or alkinyl of 3 to 6 carbon atoms, the multiple bond thereof being other than adjacent to the nitrogen atom of the tricyclic ring system, oxoalkyl of 2 to 5 carbon atoms, the oxygen atom thereof being separated by at least two carbon atoms from the nitrogen atom of the tricyclic ring system, or phenylalkyl of 7 to 10 carbon atoms, R₃ is hydrogen or alkyl of 1 to 4 carbon atoms, and R₄ is hydrogen or alkyl of 1 to 4 carbon atoms, or a pharmaceutically acceptable acid addition salt thereof.

2. A pharmaceutical composition comprising an effective amount of a compound of claim 1 in association with a pharmaceutically acceptable diluent or carrier.

3. A method of treating depressions in animals, which comprises administering a therapeutically effective amount of a compound of claim 1 to an animal in need of such treatment.

4. A compound of claim 1, in which the 4a, 11a ring junction is in the trans configuration.

5. A compound of claim 1, in which the 4a, 11a ring is in the cis configuration.

6. A compound of claim 1, in which R₁ is hydrogen.

7. A compound of claim 1, in which R₂ is hydrogen or alkyl of 1 to 4 carbon atoms.

8. A compound of claim 1, in which R₃ is hydrogen or methyl.

9. A compound of claim 1, in which R₄ is hydrogen or methyl.

10. The compound of claim 1 which is trans-2,3,4,4a,11,11a-hexahydro-2-methyl-1H-benzo[5,6-]cyclohepta[1,2-c]pyridine.

11. The compound of claim 1 which is cis-2,3,4,4a,11,11a-hexahydro-2-methyl-1H-benzo[5,6-]cyclohepta[1,2-c]pyridine.

12. The compound of claim 1 which is trans-2,3,4,4a,11,11a-hexahydro-2,6-dimethyl-1H-benzo[5,6]cyclohepta[1,2-c]pyridine.

13. The compound of claim 1 which is trans-2,3,4,4a,11,11a-hexahydro-2,6-trimethyl-1H-benzo[5,6]cyclohepta[1,2-c] pyridine.

14. The compound of claim 1 which is trans-2,3,4,4a,11,11a-hexahydro-6-methyl-1H-benzo[5,6-]cyclohepta[1,2,-c]pyridine.

15. The compound of claim 1 which is trans-2,3,4,4a,11,11a-hexahydro-1H-benzo[5,6]cyclohepta[1,2,-c]pyridine-2-propan-2-one.

16. The compound of claim 1 which is trans-2-cyclopropylmethyl-2,3,4,4a,11,11a-hexahydro-1H-benzo[5,6]cyclohepta [1,2-c]pyridine.

17. The compound of claim 1 which is cis-2,3,4,4a,11,11a-hexahydro-2,6-dimethyl-1H-benzo[5,6]cyclohepta[1,2-c]pyridine.

18. The compound of claim 1 which is trans-2,3,4,4a,11,11a-hexahydro-1H-benzo[5,6]cyclohepta[1,2-c]pyridine.

19. The compound of claim 1 which is cis-2,3,4,4a,11,11a-hexahydro-6-methyl-1H-benzo[5,8-]cyclohepta[1,2-c]pyridine.

20. The compound of claim 1 which is trans-2,3,4,4a,11,11a-hexahydro-2-ethyl-6-methyl-1H-benzo[5,6]cyclohepta [1,2-c]pyridine.

21. The compound of claim 1 which is trans-2,3,4,4a,11,11a-hexahydro-2-i-propyl-6-methyl-1H-benzo[5,6]cyclohepta[1,2-c]pyridine.

22. The compound of claim 1 which is trans-2,3,4,4a,11,11a-hexahydro-2,5-dimethyl-1H-benzo[5,6]cyclohepta [1,2-c]pyridine.

23. The compound of claim 1 which is cis-2,3,4,4a,11,11a-hexahydro-2,5-dimethyl-1H-benzo[5,6]-cyclohepta[1,2-c] pyridine.

24. The compound of claim 1 which is trans-2,3,4,4a,11,11a-hexahydro-8-methyl-1H-benzo[5,6-]cyclohepta[1,2-c]pyridine.

25. The compound of claim 1 which is trans-2,3,4,4a,11,11a-*hexahydro*-2-methyl-8-chloro-1H-benzo[5,6]cyclohepta [1,2-c]pyridine.

26. The compound of claim 1 which is trans-2,3,4,4a,11,11a-hexahydro-2,6-dimethyl-8-chloro-1H-benzo[5,6]cyclohepta[1,2-c]pyridine.

27. The compound of claim 1 which is trans-2,3,4,4a,11,11a-hexahydro-2-benzyl-6-methyl-1H-benzo[5,6]cyclohepta [1,2-c]pyridine.

28. The compound of claim 1 which is trans-2,3,4,4a,11,11a-hexahydro-2-phenethyl-1H-benzo[5,6]cyclohepta[1,2-c]pyridine.

29. The compound of claim 1 which is trans-2,3,4,4a,11,11a-hexahydro-2-phenethyl-6-methyl-1H-benzo[5,6]cyclohepta[1,2-c]pyridine.

* * * * *